United States Patent
Kusnezoff et al.

(10) Patent No.: US 8,368,411 B2
(45) Date of Patent: Feb. 5, 2013

(54) METHOD FOR DETERMINING DIFFUSION AND/OR TRANSFER COEFFICIENTS OF A MATERIAL

(75) Inventors: Mihails Kusnezoff, Dresden (DE); Steffen Ziesche, Dresden (DE); Anne Paepke, Dresden (DE)

(73) Assignee: Fraunhofer-Gesellschaft zur Foerderung der Angewandten Forschung E.V, Munich (DE)

( * ) Notice: Subject to any disclaimer, the term of this patent is extended or adjusted under 35 U.S.C. 154(b) by 214 days.

(21) Appl. No.: 12/452,994

(22) PCT Filed: Jul. 28, 2008

(86) PCT No.: PCT/DE2008/001283
§ 371 (c)(1),
(2), (4) Date: Apr. 19, 2010

(87) PCT Pub. No.: WO2009/015662
PCT Pub. Date: Feb. 5, 2009

(65) Prior Publication Data
US 2010/0207646 A1    Aug. 19, 2010

(30) Foreign Application Priority Data
Jul. 30, 2007   (DE) .................. 10 2007 037 203

(51) Int. Cl.
*G01R 27/08*   (2006.01)
*G01N 27/02*   (2006.01)
(52) U.S. Cl. ........ 324/693; 324/713; 324/439; 324/441; 324/444
(58) Field of Classification Search .................. 324/439, 324/441, 444, 446, 691, 693, 713
See application file for complete search history.

(56) References Cited

U.S. PATENT DOCUMENTS 4,510,036 A * 4/1985 Takeuchi et al. .............. 204/425
(Continued)

FOREIGN PATENT DOCUMENTS

DD    132 687    10/1978

OTHER PUBLICATIONS

L. Chen et al., Electrical Conductivity Relaxation Studies of Oxygen Transport in Epitaxial YBCO Thin Films, Jun. 2003, IEEE Transactions on Applied Superconductivity, vol. 13, No. 2, pp. 2882-2885.*

(Continued)

*Primary Examiner* — Timothy J Dole
(74) *Attorney, Agent, or Firm* — Jacobson Holman PLLC

(57) ABSTRACT

The invention relates to a method for the determination of diffusion coefficients and/or exchange coefficient of a material having electronic and ionic conductivity. The material is permeable to at least one gas. It is the object of the invention to provide a cost-effective, accurate method for the determination of the diffusion coefficient and of the surface exchange coefficient which can be carried out in a short time and can thus be used for a screening of materials, in particular for application in the field of permeation membranes. The procedure is followed in accordance with the invention such that a sample of the material is arranged in a measurement chamber and has an electric current passed through it for a determination of the electric resistance. In this respect, a gas mixture in which the respective gas is contained is conducted through the measurement chamber as a gas flow and the partial pressure of the respective gas in the gas mixture is changed periodically at regular intervals. The change in the electric resistance of the sample is measured and a diffusion coefficient and/or exchange coefficient of the material can be determined for the respective gas from the determined change in the electric resistance.

15 Claims, 7 Drawing Sheets

System for the periodic change of the partial pressure of oxygen with simultaneous electrical measurements at the sample

U.S. PATENT DOCUMENTS

| | | | |
|---|---|---|---|
| 4,574,264 A * | 3/1986 | Takahashi et al. | 338/34 |
| 4,953,387 A * | 9/1990 | Johnson et al. | 73/25.03 |
| 5,627,479 A * | 5/1997 | Viscor et al. | 324/719 |
| 6,691,554 B2 * | 2/2004 | Eastman et al. | 73/25.03 |
| 7,003,405 B1 * | 2/2006 | Ho | 702/32 |
| 7,229,593 B1 * | 6/2007 | Ho | 422/83 |
| 7,588,626 B2 * | 9/2009 | Gopalan et al. | 95/45 |
| 2005/0252789 A1 | 11/2005 | Fray et al. | |

OTHER PUBLICATIONS

R.A. De Souza et al.; Oxygen exchange and diffusion measurements: The importance of extracting the correct initial and boundary conditions; Solid State Ionics, vol. 176 (2005); pp. 1915-1920.

M. Søgaard et al.; Oxygen nonstoichiometry and transport properties of strontium substituted lanthanum cobaltite; Solid State Ionics, vol. 177 (2006); pp. 3285-3296.

Preis et al.: "Oxygen exchange kinetics of La0.4Sr0.6FeO3-delta by simultaneous application of conductivity relaxation and carrier gas coulometry"; Solid State Ionics, vol. 175, No. 1-4, Nov. 30, 2004, pp. 393-397.

Closset et al.: "Study of oxygen exchange and transport in mixed conducting electroceramics", Journal of the European Ceramic Society, vol. 19, No. 6-7, Jun. 1, 1999, pp. 843-846.

Izu et al.: "Evaluation of response characteristics of resistive oxygen sensors based on porous cerium oxide thick film using pressure modulation method", Sensors & Actuators B, Elsevier Sequoia S.A., vol. 113, No. 1, Jan. 17, 2006, pp. 207-213.

Mauvy et al.: Measurement of chemical and tracer diffusion coefficients of oxygen La2Cu0.5Ni0.5O4+delta; Solid State Ionics, vol. 158, No. 3-4, Mar. 1, 2008, pp. 395-407.

Sitte et al.: "Nonstoichimetry and transport properties of strontium-substituted lanthanum cobaltites", Solid State Ionics, vol. 154-155, Dec. 2, 2002, pp. 517-522.

Sahibzada et al.: "A simple method for the determination of surface exchange and ionic transport kinetics in oxides", Solid State Ionics, vol. 136-137, Nov. 2, 2000, pp. 991-996.

Burgermeister et al.: "Electrochemical device for the precise adjustment of oxygen partial pressures in a gas stream"; Solid State Ionics, vol. 170, No. 1-2, May 14, 2004, pp. 99-104.

Lade et al.: "Deformation and kinetic transport parameters for oxygen in mixed conductors by an ac method:" Solid State Ionics, vol. 72, Pt. 2, Sep. 12, 1993, pp. 218-223.

Tragut: "The influence of the surface transfer reaction on the response characteristics of resistive oxygen sensors"; Sensors and Actuators, vol. B7, No. 1-3, Mar. 1992, pp. 742-746.

Izu et al.: "Evaluation of response characteristics of resistive oxygen sensors using Ce0.9Zr0.1O2 thick film by pressure modulation method"; Sensors and Actuators, vol. 130, No. 1, Mar. 10, 2008, pp. 466-469.

* cited by examiner

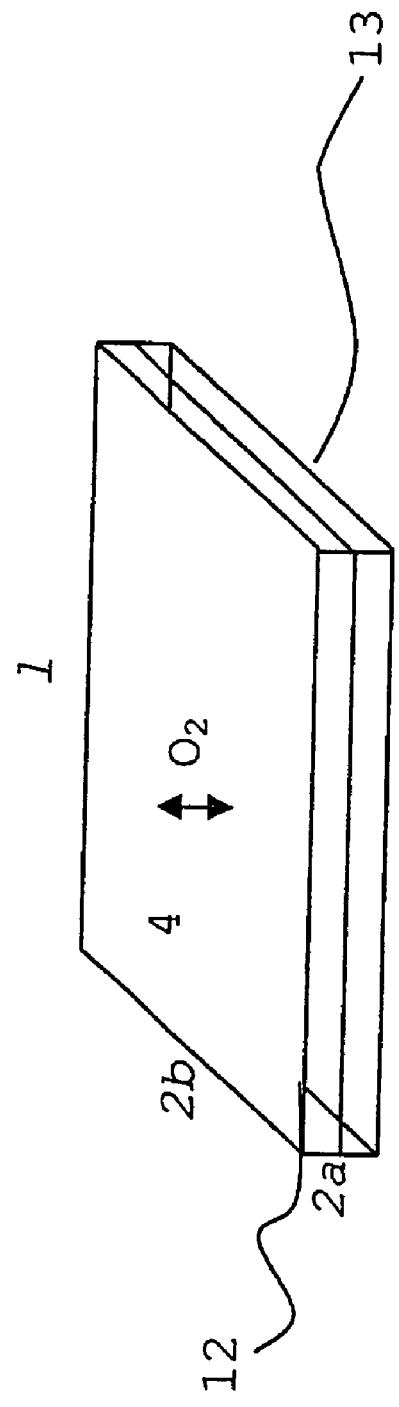
Figure 1: Sample for resistance determination with pick-ups for current and voltage measurement

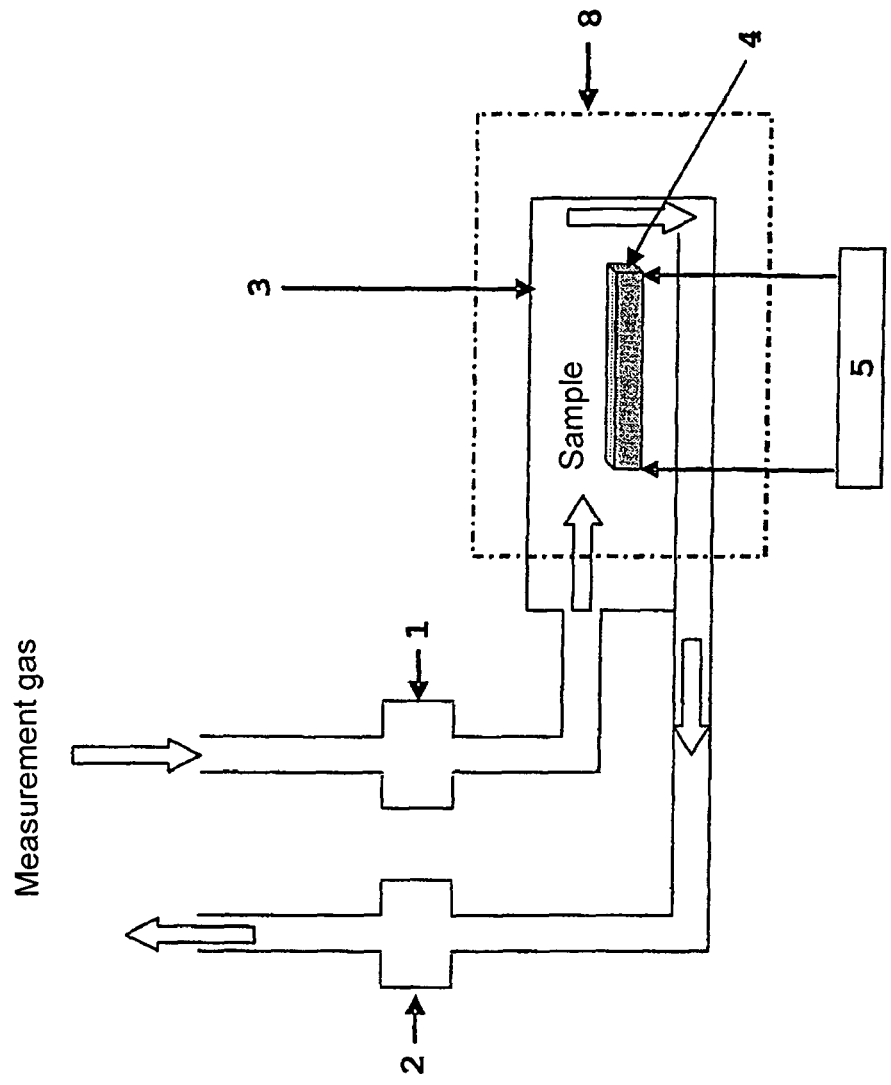
Figure 2: System for the periodic change of the partial pressure of oxygen with simultaneous electrical measurements at the sample

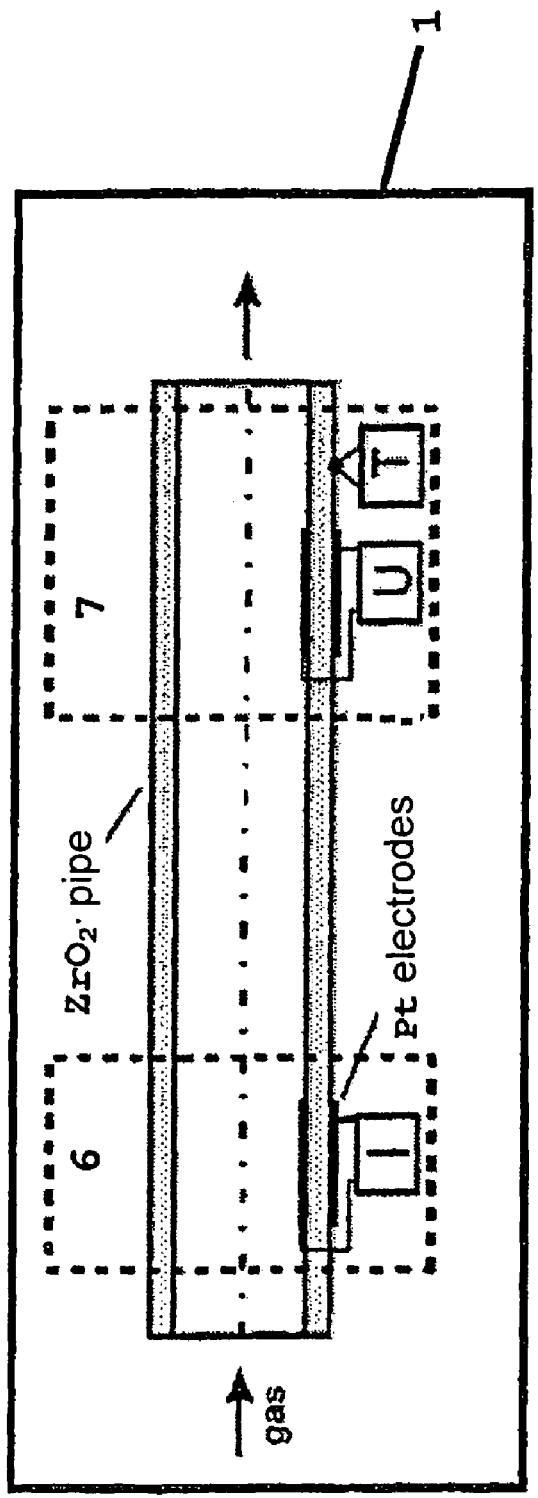
Figure 3: Schematic representation of the solid electrolyte cell utilized for the setting of the periodic changes in the gas partial pressure.

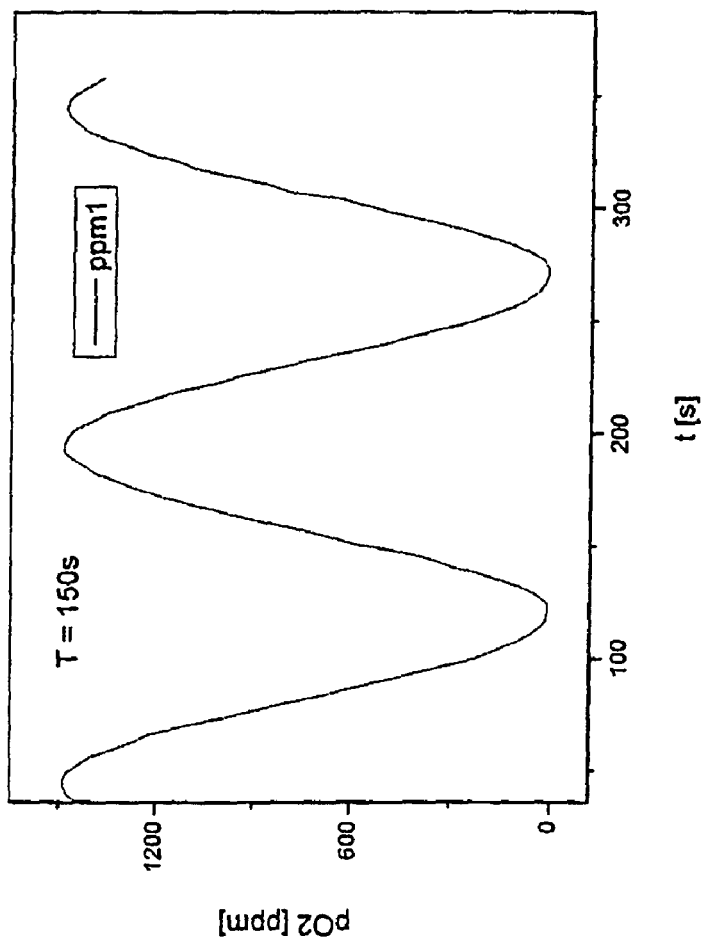
Figure 4: Periodic change in the partial pressure of oxygen in the measurement gas (period length 150 s), caused by the periodic change in the electric current at the part of the solid electrolyte cell 1 acting as an oxygen pump

Figure 5: Reached amplitudes of the partial pressure of oxygen in dependence on the frequency with a base content of 750 ppm $O_2$ in the measurement gas and a target amplitude of 1450 ppm and 0 ppm $O_2$ respectively (the target amplitude is 99% reached at T > 50 s)
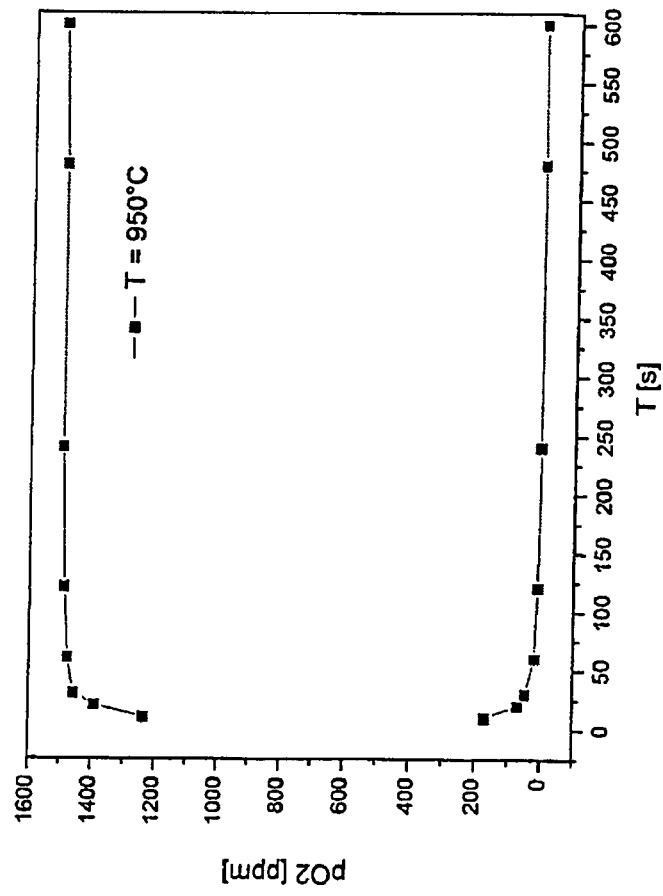

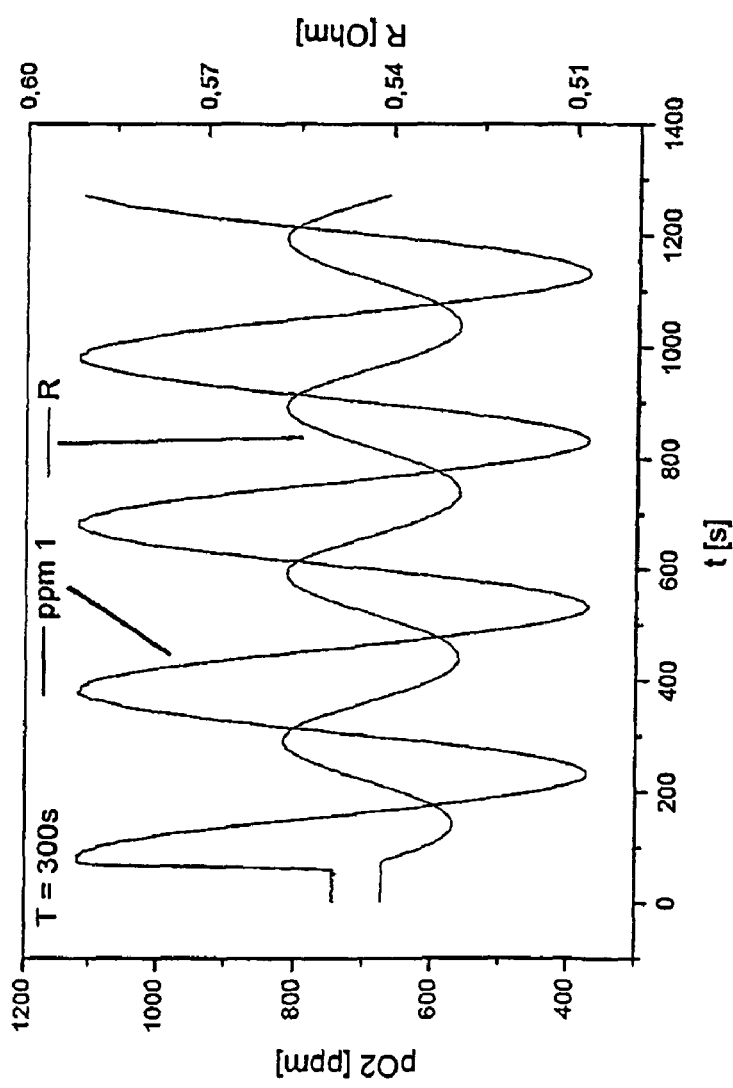
Figure 6: Resistance change in the sample (blue) in dependence on the partial pressure of oxygen in the measurement gas (black)

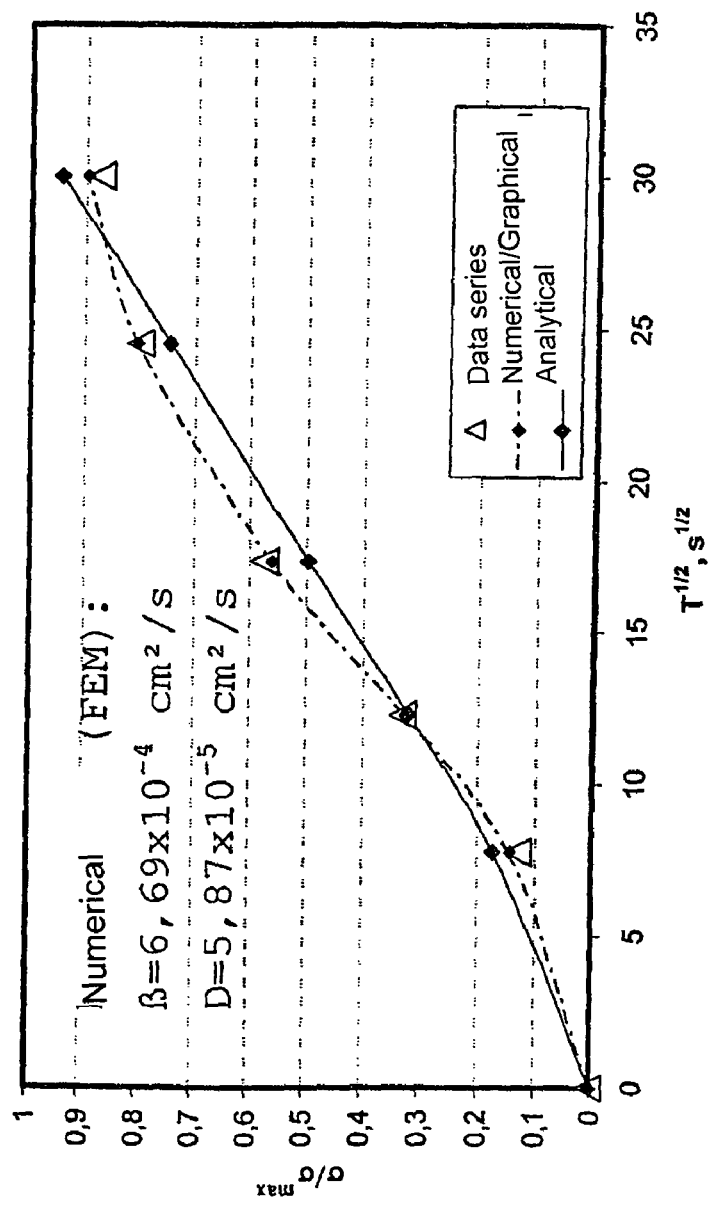
Figure 7: Dependence of the amplitude of the resistance change on the period and determination of the exchange coefficient and diffusion coefficient by means of analytical and FEM calculation

METHOD FOR DETERMINING DIFFUSION AND/OR TRANSFER COEFFICIENTS OF A MATERIAL

This is a national stage of PCT/DE08/001,283 filed Jul. 28, 2008 and published in German, which has a priority of German no. 10 2007 037 203.7 filed Jul. 30, 2007, hereby incorporated by reference.

The invention relates to a method for the determination of the diffusion coefficient and/or exchange coefficient of a material having electronic and ionic conductivity. The material is permeable to at least one gas.

Permeation membranes, in particular oxygen permeation membranes, represent a cost-effective alternative for the recovery of a gas, e.g. for the recovery of oxygen from air. Materials having electronic conductivity, and in particular high ionic conductivity, (mixed conductors) are used as the materials for the manufacture of such membranes. Two specific parameters are important for the ion exchange of the gas (oxygen ion transport) through the membrane: Ionic conductivity (determined by the chemical diffusion coefficient for the respective gas) and surface exchange (determined by the chemical surface exchange coefficient). These two values can currently only be determined by complex isotope exchange experiments (specifically: Isotope exchange depth profiling (IEDP)—R. A. De Souza, R. J. Chater, Solid State Ionics, 176 (2005) 1915-1920). For the determination of the material parameters by means of IEDP, the samples are heated to operating temperature and are charged with the gas, which contains $O^{18}$ isotopes, in a special chamber. A concentration profile of $O^{18}$ ions forms in the sample due to the oxygen exchange on the sample surface and due to the self-diffusion of the $O^{18}$ species in the lattice (caused by the concentration gradient of the $O^{18}$ oxygen species. This profile is subsequently measured using the method of secondary ion mass spectroscopy (SIMS). The parameters self-diffusion coefficient ($D^*$) and surface exchange coefficient ($k^*$) are determined by the solving of the diffusion equation using corresponding boundary conditions and the fit of the experimentally measured diffusion profile.

High installation procurement costs (approximately 1.5 m euros), a high experimental effort and long analysis times are associated with the IEDP method. For these reasons, this method is not suitable for the fast screening of different compositions of materials.

Conductivity relaxation methods and mass relaxation methods for the determination of oxygen exchange coefficients and oxygen diffusion coefficients are known from the prior art (W. Preis, E. Bucher, W. Sitte, Solid State Ionics 175 (2004) 393-397). In these methods, the change in the conductivity or in the mass of the sample is observed with a change carried out step-wise in the partial pressure of oxygen or in the sample temperature in a reactor. The disadvantage of these methods is that only diffusion coefficients with reduced accuracy can be determined from the relaxation curves and no reliable values can be obtained for the exchange coefficient (M. Sogaard, P. V. Hendriksen, M. Mogensen, F. V. Poulsen. E. Skou, Solid State Ionics 177 (2006) 3285-3296).

It is therefore the object of the invention to provide a cost-effective, accurate method for the determination of the diffusion coefficient and of the surface exchange coefficient which can be carried out in a short time and can thus be used for a screening of materials, in particular for application in the field of permeation membranes.

In accordance with the invention, this object is solved by a method having the features of claim 1. Advantageous embodiments and further developments of the invention can be achieved using features designated in the subordinate claims.

In accordance with the invention, the procedure is that a sample of the material is arranged in a measurement chamber. The sample is connected to an electric voltage source and a flow of electric current is passed through it. The respective electric resistance of the sample is measured in so doing. In this respect, both electric DC current and AC current (impedance spectroscopy) can be used for the determination of the electric resistance.

A gas mixture flows through the measurement chamber. The respective gas is contained in the gas mixture. When the gas mixture flows past the sample through the measurement chamber, the partial pressure of the respective gas is changed periodically at regular intervals and the change in the electric resistance of the sample is measured in this process. The diffusion coefficient and/or exchange coefficient of the material can be determined from the determined change in the electric resistance.

The change in the gas partial pressure can be carried out with a preset frequency at a constant amplitude around a mean value. These two parameters can be optimized for a respective material and/or for a respective gas. They should be kept constant in a determination. The change in the partial pressure should take place in a sinusoidal manner. In this respect, a period length of at least 0.5 s, preferably of at least 5 s, particularly preferably of at least 10 s should be achievable. The amplitude at which the change of the partial pressure is carried out should be at least 15 ppm.

The change in the partial pressure should be carried out at a plurality of preset frequencies, preferably at least five frequencies.

A gas mixture should be used which contains at least one component which is selected from the gases oxygen, hydrogen, water vapor, carbon monoxide, carbon dioxide, nitrogen and argon.

The method in accordance with the invention is in particular suitable for the determination of diffusion coefficients and/or exchange coefficients for oxygen or hydrogen as the respective gas contained in a gas mixture. With oxygen, a gas mixture can advantageously be used which is formed with oxygen and nitrogen. For hydrogen, a gas mixture can be favorable which is formed with hydrogen, water vapor and/or nitrogen.

In the determination, the sample should be heated to a temperature of at least 500° C. in the measurement chamber. A heating to temperatures above 800° C. can, however, also take place.

Even a small periodic change in the partial pressure of the respective gas at a preset frequency results in an excitation of a periodic oscillation of the electric voltage of a sample through which electric current is passed. The electric voltage oscillations take place with a gas emission/reception from the environment due to the change in the electronic conductivity of the sample. Due to the variation of the frequency, the amplitude of the electric voltage frequency changes since only the regions of the sample close to the surface are affected by the change of the gas content in the gas mixture at high frequencies.

The change in the gas content in the gas phase due to the gas emission/reception of the respective gas by the sample can be determined simultaneously at the gas outlet from the measurement chamber to determine the change in the gas content in the sample.

On a reduction in the frequency at which the change in the partial pressure is carried out, the gas content change propagates more and more deeply into the sample and thereby causes larger and larger electric conductivity changes.

The dependency of the amplitude of the electric voltage changes on the frequency of the partial pressure fluctuations is recorded for the determination of the material parameters. The maximum change in the electric conductivity can be determined particularly advantageously with a very long period of the partial pressure change of the respective gas in the gas mixture flowing through the measurement chamber or by a step-wise change in the partial pressure.

The calculation of the diffusion coefficient and of the exchange coefficient takes place by the mathematical solving of the following differential equation:

$$\frac{\partial}{\partial t}\Delta c(t, x, y, z) - \nabla \cdot (D\nabla(\Delta c(t, x, y, z))) = 0$$

with the following boundary conditions
$D\partial_N(\Delta c) = \beta(\Delta c - \Delta c_0 \sin(\omega t))$ at the sample margin
$D\partial_N(\Delta c) = 0$ at the sample center.

In these equations, $\Delta c$ is the gas concentration change as a function of time and of the spatial coordinates in the sample, D—chemical diffusion coefficient for the respective gas and β—exchange coefficient of the sample with the gas atmosphere.

In the case in which the relation sample length>sample width>>sample thickness ($2a$) is observed, the differential equation can be reduced to a one-dimensional case and can be solved analytically.

$$\frac{\partial}{\partial t}\Delta c - D\frac{\partial^2 \Delta c}{\partial x^2} = 0$$

$$-D\frac{\partial \Delta c}{\partial x}\bigg|_{x=a} = \beta(\Delta c - \Delta c_0 \sin(\omega t))$$

at the sample surface $$-D\frac{\partial \Delta c}{\partial x}\bigg|_{x=0} = 0$$

at the sample center.
For the case $k\alpha = (\omega/2D)^{1/2}\alpha \gg 1$:

$$\Delta c(x, t) = \Delta c_0 \cdot e^{-k(a-x)}\left\{\frac{1+(1+2h_0 k)}{1+(1+2h_0 k)^2}\sin(\omega t + k(a-x)) + \frac{2h_0 k}{1+(1+2h_0 k)^2}\cos(\omega t + k(a-x))\right\}$$

results as the analytical solution
with 2a—sample thickness $k = (\omega/2D)^{1/2}$ $h_0 = -D/\beta$.

The change in the partial pressure in the gas mixture (atmosphere surrounding the sample) results in electric conductivity changes in the material to be examined. The change in the electric conductivity, which is in turn caused by the change in the charge carrier concentration in the material, can be calculated from the change in this concentration. If this only changes slightly, the change in the electric conductivity is proportional to the change in the charge carrier concentration as a consequence of the partial pressure change of the respective gas in the gas mixture. The maximum change in the electric conductivity is produced when the gas exchange of the sample takes place such that it is in balance with the composition of the gas mixture with a changed instantaneous partial pressure. As is illustrated with FIG. 1, the maximum change of the electric conductivity can be calculated by $$\Delta S^{max} = \frac{2a \cdot 2b}{l}\Delta S_0 = \frac{2a \cdot 2b}{l}\mu_e q\Delta c_0$$

On the periodic change of the concentration of the respective gas in the gas mixture, the electric conductivity change can be calculated from the following equation:

$$\Delta S(t) = \frac{2b}{l}\int_{-a}^{a}\Delta S_0(x, t)dx = $$
$$\frac{2b}{l}\mu_e q\int_{-a}^{a}\Delta c(x, t)dx = \frac{4b}{l}\mu_e q\int_{0}^{a}\Delta c(x, t)dx = \frac{\Delta S^{max}}{a}\int_{0}^{a}\frac{\Delta c(x, t)}{\Delta c_0}dx$$

After integration of the concentration dependence, the following expression is obtained for the relative change in the amount of the electrical conductivity as a function of the period of the gas concentration change in the gas mixture:

$$\frac{|\Delta S|}{S_0^{max}} = \frac{(DT)^{1/2}}{\pi^{1/2}a}\frac{1}{(1+(1+2h_0 k)^2)^{1/2}} = \frac{(DT)^{1/2}}{\pi^{1/2}a}\frac{1}{\left(1+(1+2h_0\pi^{1/2}(DT)^{-1/2})^2\right)^{1/2}}$$

This function can be used to adapt the experimentally measured dependency $|\Delta S\Delta/S^{max}|=f(T)$ and to determine the parameters β and D (T period of the $pO_2$ fluctuations).

The invention should be explained in more detail by way of example in the following.

There are shown:
FIG. 1 a perspective representation of a sample;
FIG. 2 a block diagram of an arrangement for the carrying out of the method;
FIG. 3 a schematic representation of parts of an arrangement for the carrying out of the method;
FIG. 4 a diagram with periodically changed partial pressure of oxygen when a gas for the diffusion coefficient and/or exchange coefficient of a material should be determined;
FIG. 5 a diagram of the reached amplitudes of the partial pressure of oxygen in dependence on the frequency of the partial pressure change at a mean value of 750 ppm of oxygen in a gas mixture with nitrogen and of an amplitude to be reached of 1450 or 0 ppm respectively at a temperature of 950° C.;
FIG. 6a diagram of the curves of the change in the electric resistance of a sample in dependence of the periodically changing partial pressure in the gas mixture; and
FIG. 7 a diagram of the dependency of the amplitude of the change in the electric resistance of a sample and of the determination of the exchange coefficient and diffusion coefficient of a material which were determined analytically and by means of an FEM (finite element method) calculation.

A geometric design of a sample 4 should be illustrated by FIG. 1. The sample 4 has a sample thickness $2a$, a sample width $2b$ and a length $l$. Two connections 12 and 13 are present for an electric voltage source (not shown) and for the measurement of the electric resistance.

A suitable arrangement for the change of the partial pressure of a respective gas, e.g. of the partial pressure of oxygen, is shown schematically in FIG. 2. Nitrogen is conducted through the solid electrolyte cell 1, which has an oxygen metering pump 6 (FIG. 3) and a potentiometric oxygen measuring cell 7 (FIG. 3), at a specific oxygen partial pressure of 1000 ppm. A periodic change in the partial pressure of oxygen in the gas mixture which flows through the cell and which is formed by oxygen and nitrogen is achieved in the arrangement by the period change in the electric current at the oxygen metering pump 6 of the solid electrolyte cell 1. The periodic change of the oxygen content is measured by the oxygen measuring cell 2, which is likewise a solid electrolyte cell. It is thereby possible to set the amplitude of the partial pressure change of oxygen in the gas mixture in a defined manner with different period lengths. It should be ensured in this respect that the amplitude of the change of the partial pressure of oxygen in the actual measurement chamber 3 is independent of the period of the partial pressure change. This could only be achieved experimentally in this embodiment for periods >10 s, as is illustrated by the diagram shown in FIG. 5. In this respect, period lengths of longer than 50 s were determined as favorable with the reaching of 99% of the target amplitude.

The sample 4 having lateral dimensions 15×4.5×1.5 mm is then heated to a temperature of 950° C. in nitrogen with 1000 ppm $O_2$ and is brought into balance with this gas atmosphere (it is waited until the electric resistance of the sample 4 measured with an electric measuring device 5 remains constant). The oxygen content in the nitrogen is then lowered periodically by means of a solid electrolyte cell 1 to a value of 500 ppm. After a resistance relaxation, an electric resistance value is adopted which corresponds to the balance between the gas with the partial pressure of oxygen of 500 ppm and the sample 4.

The measurement chamber 3 with sample 4 can be arranged in an oven 8 to be able to achieve the desired temperatures in the examinations.

The gas flow of the gas mixture can be conducted through a housing which can also be a component of the measurement chamber 3. Said housing can be formed from quartz.

The measuring cell 1 can be equipped with platinum electrodes for the referencing of the gas mixture before the measurement chamber 3. As is indicated in FIG. 3.

The electric resistance change at the partial pressures of oxygen between 1000 and 500 ppm corresponds to the maximum possible change of the electric resistance at a partial pressure change of oxygen of 1000 to 500 or from 1000 to 1500 ppm ($S^{max}$). The sample 4 is then in turn brought into balance with the gas atmosphere of 1000 ppm oxygen.

In this state, the partial pressure of oxygen is changed periodically with the solid electrolyte cell 1 with a sinus function and an amplitude of 500 ppm between 500 ppm and 1500 ppm. A periodic change in the electric resistance of the sample 4 is adopted by this change. The period of the electric resistance change in this respect corresponds to the period of the generated change in the partial pressure of oxygen, as illustrated with FIG. 6. The development of the change of the electric resistance is in this respect around a mean value of $0.54\Omega$ with an amplitude of approximately $0.15\Omega$. The amplitude of the electric resistance change depends on the period of the partial pressure change of oxygen.

FIG. 7 shows results of the adaptation using the analytical formula and by means of FEM simulation as well as calculated values for the diffusion coefficient D and the surface exchange coefficient k for a $La_2Ni_{0.8}Cu_{0.2}O_4$ compound. A clear deviation of the curve for the analytical solution can be recognized at large period durations (ka>>1 is no longer satisfied and the analytical solution loses its validity). The FEM assisted calculation, in contrast, provides more accurate values for D ($5.87\times10^{-5}$ cm$^2$/s) and β ($6.69\times10^{-4}$ cm/s) which are comparable with the literature data for a similar compound (F. Mauvy, J. M. Bassat, E. Boehm, P. Dordor, J. P. Loup, Solid State Ionics 158 (2003) 395-407 gives a value for $D_{chem}$ of $3$–$10\times10^{-5}$ cm$^2$/s at 950° C. as the material $La_2Ni_{0.5}Cu_{0.5}O_4$ for the chemical compound and E. Boehm, J. M. Bassat, M. C. Steil, P. Dordor, F. Mauvy, J. C. Grenier, Solid State Sciences 5 (2003) 973-981, gives a value for δ of $5\times10^{-6}$ cm/s at 800° C. for the compound $La_2Ni_{0.75}Cu_{0.25}O_4$, which allows a value of $8\times10^{-5}$ cm/s to be calculated when the activation energy for B from this work for 950° C. is taken into account). The accuracy of the parameter determination from the fit amounts to approximately 10%, which is much better than the accuracy of the relaxation method or IEDP.

The invention claimed is:

1. A method for determining a diffusion coefficient and/or an exchange coefficient or a material having electronic and ionic conductivity, the material being permeable to at least one gas, comprising the steps of,
   arranging a sample of the material in a measurement chamber and passing an electric current through the material for determining the electric resistance of the material;
   conducting a gas mixture which contains the said gas through the measurement chamber as a gas flow;
   periodically increasing and decreasing the partial pressure of the said gas in the gas mixture at regular intervals, measuring the change in the electric resistance of the sample during both the increasing and decreasing of the partial pressure, and determining the diffusion coefficient and/or exchange coefficient of the material for the said gas from the measured change in the electric resistance.

2. A method in accordance with claim 1, characterized in that the periodic increasing and decreasing of the partial pressure of the respective gas is carried out with a constant amplitude about a mean value.

3. A method in accordance with claim 1, characterized in that the periodic increasing and decreasing of the partial pressure is carried out at a plurality of preset frequencies.

4. A method in accordance with claim 1, characterized in that the periodic increasing and decreasing of the partial pressure is carried out with a period length of more than 0.5 s.

5. A method in accordance with claim 1, characterized in that the periodic increasing and decreasing of the partial pressure is carried out sinusoidally.

6. A method in accordance with claim 1, characterized in that the electric resistance change in the sample is determined with electric direct current.

7. A method in accordance with claim 1, characterized in that the electric resistance change in the sample is determined with electric alternating current/impedance spectroscopy.

8. A method in accordance with claim 1, characterized in that the sample is heated in the measurement chamber.

9. A method in accordance with claim 8, characterized in that the sample is heated to at least 500° C.

10. A method in accordance with claim 1, characterized in that a gas mixture contains at least one component which is selected from oxygen, hydrogen, water vapor, carbon monoxide, carbon dioxide, nitrogen and argon.

11. A method in accordance with claim 1, characterized in that the diffusion coefficient and/or exchange coefficient is/are determined for oxygen.

12. A method in accordance with claim 1, characterized in that a gas mixture is used which is formed with oxygen and nitrogen.

13. A method in accordance with claim 1, characterized in that the diffusion coefficient and/or exchange coefficient is/are determined for hydrogen.

14. A method in accordance with claim 1, characterized in that a gas mixture is used which is formed with hydrogen, water vapor and/or nitrogen.

15. A method in accordance with claim 1, characterized in that the change of the partial pressure is carried out at an amplitude of at least 15 ppm.

* * * * *